United States Patent [19]

Bieser

[11] 4,006,197
[45] Feb. 1, 1977

[54] PROCESS FOR SEPARATING NORMAL PARAFFINS

[75] Inventor: Herbert J. Bieser, Des Plaines, Ill.
[73] Assignee: UOP Inc., Des Plaines, Ill.
[22] Filed: Nov. 19, 1975
[21] Appl. No.: 633,183
[52] U.S. Cl. ..................... 260/676 MS; 208/310 Z
[51] Int. Cl.² ................... C10G 25/04; C07C 7/13
[58] Field of Search .......... 260/676 MS; 208/310 Z
[56] References Cited
UNITED STATES PATENTS

| 3,306,848 | 2/1967 | Wackher et al. | 208/310 Z |
| 3,726,792 | 4/1973 | Francis et al. | 260/676 MS |

Primary Examiner—Herbert Levine
Attorney, Agent, or Firm—James R. Hoatson, Jr.; Thomas K. McBride; William H. Page, II

[57] ABSTRACT

An improved process for separating normal paraffins from a feed stream containing a mixture of normal paraffins and isoparaffins. The general process comprises the steps of contacting the feed stream with an adsorbent comprising a crystalline aluminosilicate thereby adsorbing normal paraffins and subsequently contacting the adsorbent with a desorbent material to remove the adsorbed normal paraffins. The improvement resides in a method of fractionating and recycling a desorbent material for re-use in the process in a manner that reduces total fractionation energy requirements. The method is particularly suitable when two desorbent materials are used in the process.

18 Claims, 1 Drawing Figure

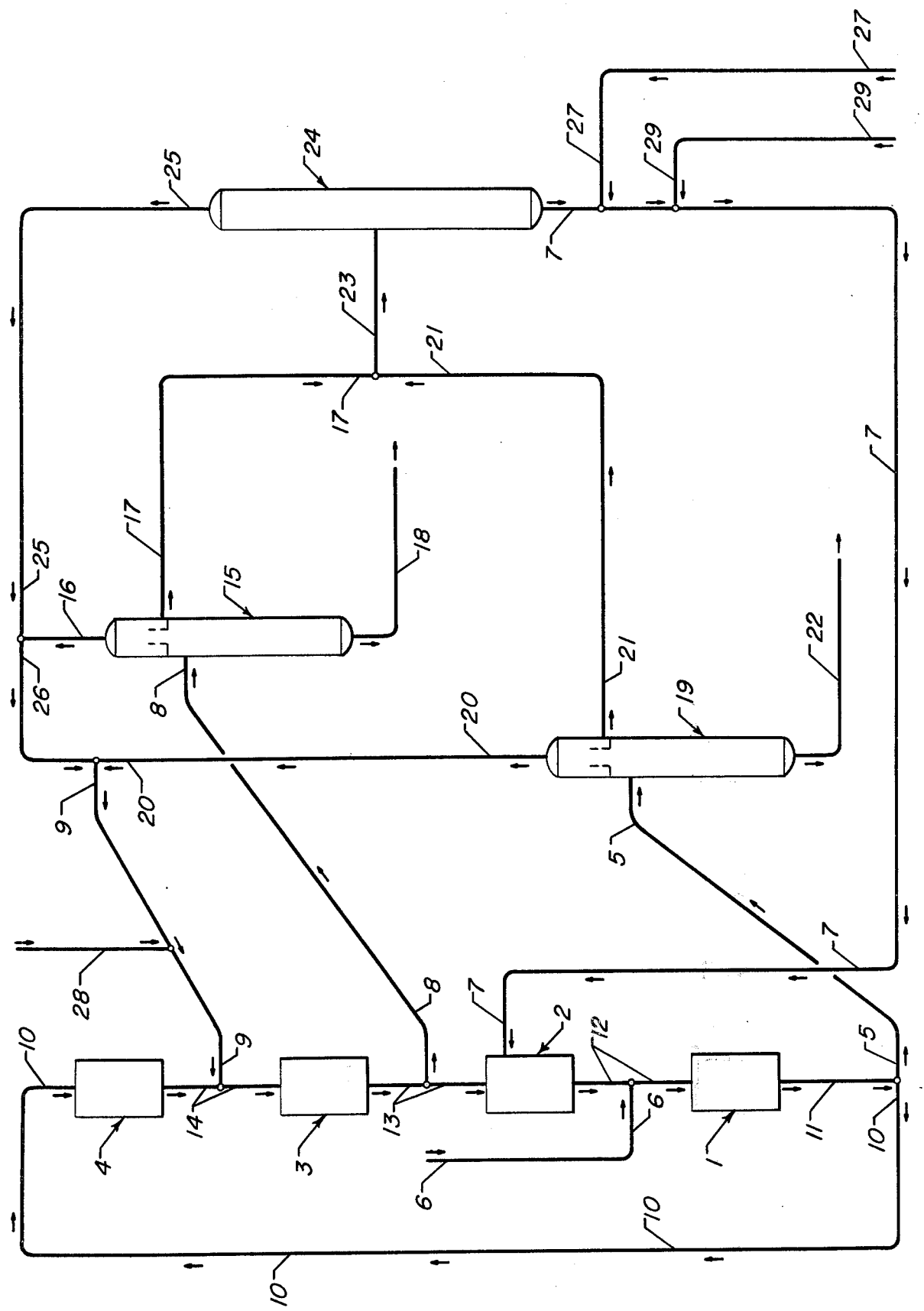

PROCESS FOR SEPARATING NORMAL PARAFFINS

BACKGROUND OF THE INVENTION

1. Field of the Invention

The field of art to which this invention pertains its hydrocarbon separation. Specifically this invention relates to an improved process which utilizes a crystalline aluminosilicate adsorbent and a desorbent to separate normal paraffins from a feed mixture containing normal paraffins. More specifically this invention relates to an improved normal paraffin separation process which employs a crystalline aluminosilicate adsorbent and a two-step desorption step to produce a high-purity normal paraffin product stream containing a reduced concentration of aromatic contaminants.

2. Description of the Prior Art

Applicant recognizes the abundance of prior art in the separation field especially that art relating to countercurrent fixed bed type operations which are commonly referred to as simulated countercurrent-flow fixed-bed type operations as particularly exemplified in U.S. Pat. No. 2,985,589.

Specific prior art patents which are considered closely related to the present invention are Broughton and Gerhold U.S. Pat. No. 2,985,589; Broughton U.S. Pat. No. 3,274,099; Pharis et al U.S. Pat. No. 3,732,325; Neuzil U.S. Pat. No. 3,696,107; Pharis et al U.S. Pat. No. 3,723,302; Adams et al U.S. Pat. No. 3,733,261; and Broughton U.S. Pat. No. 3,715,409. All of these patents relate to simulated countercurrent solid-fluid separation processes in which an extract component of a feed stream is separated by selective adsorption on a particular adsorbent and subsequently recovered as a product stream in a higher concentration than that in the feed stream. In each process there are various zones representing quantities of adsorbent material in which individual operatons are taking place. In each, at least three operational zones are utilized: an adsorption zone, a purification zone and a desorption zone. In the adsorption zone, the selectively adsorbed extract material and perhaps some contaminant materials are adsorbed while the less selectively retained raffinate materials generally remain in the interstitial void spaces surrounding the adsorbent. The basic operation taking place in the purification zone is the purification of the adsorbed extract materials present in the adsorbent; the adsorbent in "passing" through the purification zone becomes more concentrated with the extract material and less concentrated with raffinate materials. In the desorption zone a desorbent material removes the adsorbed extract material from the adsorbent.

The first patent discloses the basic concept of a simulated countercurrent solid-fluid contacting process employing a fixed bed of solid adsorbent having moving input and output streams which allow a segregation of zones in which separate functions are taking place in order to separate a feed stream into a raffinate product component and an extract product component.

The second U.S. Pat. No. 3,274,099 includes the same basic processing steps as the first patent but also includes an additional input stream into the purification zone, which is located between the adsorption zone and the desorption zone. The input stream is a sweeping agent, a raffinate-type (that is, a material which is relatively unadsorbed by the adsorbent) compound having a boiling point to permit separation by distillation from the feed raffinate component, which is passed into the process to push raffinate material which is trapped in the interstitial void spaces between adsorbent particles in the purification zone back into an adsorption zone to prevent feed raffinate material from passing from the adsorption zone through the purification zone and into a desorption zone thereby contaminating an extract product with feed raffinate material. In one embodiment, the process of U.S. Pat. No. 3,274,099 is used to separate normal paraffins from isoparaffins.

U.S. Pat. No. 3,732,325 discloses a process which employs the same basic processing steps of the first patent and a particular adsorbent to separate aromatic hydrocarbons, particularly the $C_8$ aromatics. In the process described in that patent a purification stream which comprises extract material is passed into the purification zone. The extract material can be taken either from an extract stream outlet from the process or from extract material which has been separated from desorbent material in an extract stream fractionator. The purification stream containing the extract material displaces from the interstitial void spaces between the adsorbent particles any raffinate materials carried into the purification zone, removes feed contaminants adsorbed by the adsorbent and reduces the quantity of desorbent which normally surrounds the adsorbent particles in the zone when no purification stream is used.

U.S. Pat. No. 3,696,107 discloses a process for separating para-xylene from a feed stream containing a mixture of $C_8$ aromatics which employs the basic processing steps described in the first patent, a particular crystalline aluminosilicate adsorbent and a two-stage desorption operation in which a first desorbent stream contacts adsorbent in the desorption zone to effect the desorption of para-xylene from the adsorbent and a second desorbent stream contacts the adsorbent in the desorption zone to effect the pushing of desorbed para-xylenes from the interstitital void spaces between the adsorbent particles. One extract stream is withdrawn from the process.

In U.S. Pat. No. 3,723,302, which discloses a process for separating olefins from paraffins employing the basic processing steps described in the first patent and a particular adsorbent, a two-step desorption operation is again used. The process uses two desorbent materials both of which enter into the desorption zone. The first desorbent material contacts the absorbent in the desorption zone and causes contaminants to be desorbed from the absorbent while the second desorbent material is used to desorb the product olefins from the adsorbent contained in the same desorption zone. Two extract streams are withdrawn from the process, an extract contaminant outlet stream and an extract olefin outlet stream.

U.S. Pat. No. 3,733,261 also discloses a process for separating olefins from paraffins which employs the basic processing steps of the first patent mentioned. In that process one desorbent material is admitted in two places in the desorption zone and two extract streams are removed from the process, an extract contaminant stream containing aromatic contaminants and desorbent material and an extract olefin stream containing olefins and desorbent material.

U.S. Pat. No. 3,715,409 discloses a process for the separation of aromatic hydrocarbons which employs four zones and includes the steps of: passing an extract material input stream into the purification zone to effect the desorption and displacement of raffinate material; passing at least a portion of the raffinate output stream passing out of the adsorption zone into the buffer zone to effect desorption and displacement of desorbent material; and, passing a raffinate input stream into an adsorption zone to effect displacement of desorbent from the adsorbent in that zone.

In each of the processes described above an extract output stream and the raffinate output stream generally contain a desorbent material which must be removed from at least the extract output stream to produce a high purity extract product and to allow reuse of the desorbent material. In processes where it is the extract component and not the raffinate component that is the desired product, desorbent material is nonetheless usually separated from raffinate output stream so that the desorbent material can be reused in the process. Separation is typically done in fractionation means; at least a portion of the extract output stream and of the raffinate output stream are passed to respective fractionation means wherein desorbent material is separated to produce an extract product and a raffinate product essentially free of desorbent materials and a stream from each fractionation means containing one or more desorbent materials and a sweeping agent, if one is used in the process. In processes in which only one desorbent material and no sweeping agent is employed the streams can be combined with no further processing for reuse in the process. When more than one desorbent material or a desorbent material and a sweeping agent is used in the process these desorbent-containing streams must usually be further processed to separate the desorbent materials or a desorbent material from a sweeping agent. Prior to my invention this is done by passing at least one of the desorbent-containing streams from the extract-output-stream and raffinate-output-stream fractionation means to another fractionation means, a desorbent splitter, where the separation takes place to produce streams which can be recycled to different locations in the process.

The process of my invention relates to an improved process for separating normal paraffins from a feed stream containing normal paraffins and isoparaffins. Normal paraffins are used as raw materials to make a variety of products including straight-chain olefins and alcohols, proteins intended for animal or human consumption, and detergents. The improved process in one embodiment employs in combination a crystalline aluminosilicate adsorbent, a simulated moving-bed countercurrent processing scheme, a sweeping agent and a desorbent material to effect the separation of normal paraffins while another embodiment employs in combination the same adsorbent, processing scheme, sweeping agent and two desorbent materials to produce a normal paraffin product having a reduced concentration of aromatic contaminants. The improvement comprises a method of separating a desorbent material and a sweeping agent and recycling each for reuse in the process. The improvement permits a reduction in the size of the desorbent splitter and in the energy input required to operate the splitter over the size and energy input requirement for a splitter operated without the method.

SUMMARY OF THE INVENTION

It is accordingly a broad objective of the process of my invention to provide a more economical process for separating normal paraffins from isoparaffins when the process employs a sweeping agent and one or more desorbent materials. More specifically it is an objective of my invention to provide a process for separating normal paraffins from isoparaffins having a reduced initial plant investment and a reduced operating expense over the prior art process employing a sweeping agent and one or more desorbent materials.

In brief summary my invention is, in one embodiment, an improved process for the separation of normal paraffins from a feed stream comprising a mixture of normal paraffins and isoparaffins which process employs an adsorbent comprising a shape-selective zeolite and comprises the steps of: (a) maintaining net fluid flow through a column of an adsorbent in a single direction, which column contains at least three zones having separate operational functions occurring therein and being serially interconnected with the terminal zones of said column connected to provide a continuous connection of said zones; (b) maintaining an adsorption zone in said column, said zone defined by the adsorbent located between a feed input stream at an upstream boundary of said zone and a raffinate output stream at a downstream boundary of said zone; (c) maintaining a purification zone immediately upstream from said adsorption zone, said purification zone defined by the adsorbent located between an extract output stream at an upstream boundary of said purification zone and said feed input stream at a downstream boundary of said purification zone, said purification zone having a sweeping agent input stream located upstream from said feed input stream; (d) maintaining a desorption zone immediately upstream from said purification zone, said desorption zone defined by the adsorbent located between a desorbent input stream at an upstream boundary of said zone and said extract output stream at a downstream boundary of said zone; (e) passing a sweeping agent comprising a raffinate-type compound into said purification zone; (f) passing said feed stream into said adsorption zone at adsorption conditions to effect the selective adsorption of said normal paraffins by said adsorbent and withdrawing a raffinate output stream comprising isoparaffins, sweeping agent and a hereinafter described desorbent material from said adsorption zone; (g) passing a desorbent material into said desorption zone at desorption conditions to effect the displacement of normal paraffins from the adsorbent in said desorption zone and withdrawing an extract output stream comprising normal paraffins, sweeping agent and desorbent material from said desorption zone; (h) passing at least a portion of said extract output stream to a first fractionation means and therein fractionating at first fractionating conditions said extract output stream to produce a first overhead stream comprising a mixture of sweeping agent and desorbent material and a first bottoms fraction comprising normal paraffins; (i) passing at least a portion of said raffinate output stream to a second fractionation means and therein fractionating at second fractionating conditions said raffinate output stream to produce a second overhead stream comprising a mixture of sweeping agent and desorbent material and a second bottom fraction comprising isoparaffins; (j) separating in a third fractionation means maintained at third fractionating conditions a mixture of sweeping agent and desorbent material to produce a third overhead stream comprising desorbent material and a third bottoms fraction comprising sweeping agent; (k) recycling at least a portion of said third overhead stream to said desorption zone; (l) recycling at least a portion of said third bottoms fraction to said purification zone; (m) periodically advancing through said column of adsorbent particles in a downstream direction with respect to fluid flow in said adsorption zone the feed input stream, raffinate output stream, desorbent input stream and extract output stream to effect the shifting of zones through said mass of adsorbent and the production of extract output and raffinate output streams, wherein the improvement comprises a fractionating and recycle method which comprises the steps of: (i) removing a side cut stream comprising sweeping agent and desorbent material from said first or second fractionation means, said side cut stream containing a lower concentration of desorbent material than either said first overhead stream or said second overhead stream; (ii) passing at least a portion of said side cut stream to said third fractionation means maintained at fractionating conditions and therein separating said side cut stream to produce said third overhead stream and said third bottoms fraction, and (iii) passing in admixture at least a portion each of said third overhead stream, said first overhead stream and said second overhead to said desorption zone.

In another embodiment my invention is an improved process for the separation of normal paraffins from a feed stream comprising a mixture of normal paraffins, isoparaffins and aromatic hydrocarbons which process employs an adsorbent comprising a 5A zeolite and comprises the steps of: (a) maintaining net fluid flow through a column of an adsorbent in a single direction, which column contains at least three zones having separate operational functions occurring therein and being serially interconnected with the terminal zones of said column connected to provide a continuous connection of said zones; (b) maintaining an adsorption zone in said column, said zone defined by the adsorbent located between a feed input stream at an upstream boundary of said zone and a raffinate output stream at a downstream boundary of said zone; (c) maintaining a purification zone immediately upstream from said adsorption zone, said purification zone defined by the adsorbent located between an extract output stream at an upstream boundary of said purification zone and said feed input stream at a downstream boundary of said purification zone, said purification zone having a sweeping agent input stream located upstream from said feed input stream; (d) maintaining a desorption zone immediately upstream from said purification zone, said desorption zone defined by the adsorbent located between a desorbent input stream at an upstream boundary of said zone and said extract output stream at a downstream boundary of said zone; (e) passing said feed stream into said adsorption zone at adsorption conditions to effect the selective adsorption of normal paraffins and aromatics by adsorbent in said zone; (f) passing into said purification zone a mixture of a first desorbent material and a sweeping agent and therein desorbing at first desorption conditions aromatics from the adsorbent; (g) withdrawing from said adsorption zone a raffinate output stream comprising feed isoparaffins and aromatic hydrocarbons, sweeping agent and first desorbent material; (h) passing a desorbent input stream comprising second desorbent material into said desorption zone and therein desorbing at second desorption conditons normal paraffins from the adsorbent; (i) withdrawing an extract output stream comprising normal paraffins, sweeping agent and second desorbent material from said desorption zone; (j) passing at least a portion of said extract output stream to a first fractionation means and therein fractionating at first fractionation condition said extract output stream to produce a first overhead stream comprising a mixture of sweeping agent, first desorbent material, and second desorbent material and a first bottoms fraction comprising normal paraffins; (k) passing at least a portion of said raffinate output stream to a second fractionation means and therein fractionating at second fractionating conditions said raffinate output stream to producre a second overhead stream comprising a mixture of sweeping agent, first desorbent material and second desorbent material and second bottoms fraction comprising isoparaffins and feed aromatics; (1) separating in a third fractionation means maintained at third fractionating conditons a mixture of sweeping agent, first desorbent material and second desorbent material to produce a third overhead stream comprising sweeping agent and second desorbent material and a third bottoms fraction comprising sweeping agent and first desorbent material; (m) recycling at least a portion of said third overhead stream to said desorption zone; (n) recycling at least a portion of said third bottoms fraction to said purification zone; (o) periodically advancing through said column of adsorbent particles in a downstream direction with respect to fluid flow in said adsorption zone the feed input stream, raffinate output stream, desorbent input stream and extract output stream to effect the shifting of zones through said mass of adsorbent and the production of extract output and raffinate output streams, wherein the improvement comprises a fractionating and recycle method which comprises the steps of: (i) removing a side cut stream comprising sweeping agent and first desorbent material from said first or second fractionation means, said side cut stream containing a lower concentraton of second desorbent material than either said first overhead stream or said second overhead stream; (ii) passing at least a portion of said side cut stream to said third fractionation means maintained at fractionating conditions and therein separating said side cut stream to produce said third overhead stream and said third bottoms fraction; and, (iii) passing a mixture of at least a portion each of said first overhead stream, said second overhead stream and said third overhead to said desorption zone.

Other objects and embodiments of the present invention encompass details about feed mixtures, adsorbents, desorbent materials and operating conditions all of which are hereinafter disclosed in the following discussion of each of the facets of the present invention.

DESCRIPTION OF THE INVENTION

In order to gain a better understanding of the process of this invention, the following definitions of terms that are used throughout this specification are given.

The term "feed stream" indicates a stream in the process through which feed material passes to the adsorbent. A feed material comprises one or more extract components and one or more raffinate components. An "extract component" is a compound or type of compound that is more selectively adsorbed by the adsorbent while a "raffinate component" is a compound or type of compound that is less selectively adsorbed. In this process normal paraffins from the feed stream are extract components while feed stream isoparaffins and most of the aromatics are raffinate components. A small portion of the feed aromatics are adsorbed on the surfaces of adsorbent particles, however, and thus may be considered as an extract component in the strict sense of the term. Usually the term extract component as used herein refers to a more selectively adsorbed compound or type of compound which is to be the desired product, such as normal paraffins in this process. The term "desorbent material" shall mean generally a material capable of desorbing an extract component. Specifically, the term "first desorbent material" shall mean a material capable of desorbing the surface-adsorbed feed aromatics but not capable of desorbing adsorbed normal paraffins from the adsorbent while the term "second desorbent material" shall refer to a desorbent material chosen to desorb adsorbed normal paraffins. The term "sweeping agent" shall mean a raffinate-type compound admitted to the process for the primary purpose of flushing raffinate components from the non-selective void volume (hereinafter defined) of the adsorbent. The term "desorbent stream" or "desorbent input stream" indicates the stream through which desorbent material passes to the adsorbent. The term "raffinate stream" or "raffinate output stream" means a stream through which most of the raffinate components are removed from the adsorbent. The composition of the raffinate stream can vary from about 100% desorbent material to essentially 100% raffinate components. The term "extract stream" or "extract output stream" shall mean a stream through which an extract material which has been desorbed by a desorbent material is removed from the adsorbent. The composition of the extract stream can also vary from about 100% desorbent material to essentially 100% extract components.

Although it is possible by the process of this invention to produce high purity (99+%) normal paraffins at high recoveries (90% or higher), it will be appreciated that an extract component is never completely adsorbed by the adsorbent, nor is a raffinate component completely non-adsorbed by the adsorbent. Therefore, small amounts of a raffinate component can appear in the extract stream and, likewise, small amounts of an extract component can appear in the raffinate stream. The extract and raffinate streams then are further distinguished from each other and from the feed mixture by the ratio of the concentrations of an extract component and a raffinate component appearing in the particular stream. More specifically, the ratio of the concentration of the adsorbed normal paraffins to that of the non-adsorbed isoparaffins will be lowest in the raffinate stream, next highest in the feed mixture, and the highest in the extract stream. Likewise, the ratio of the concentration of the non-adsorbed isoparaffins to that of the adsorbed normal paraffins will be highest in the raffinate stream, next highest in the feed mixture, and the lowest in the extract stream.

The term "selective pore volume" of the adsorbent is defined as the volume of the adsorbent which selectively adsorbs extract components from the feed stock. The term "non-selective void volume" of the adsorbent is the volume of the adsorbent which does not selectively retain extract components from the feed stock. This volume includes the cavities of the adsorbent which contain no adsorptive sites and the interstitial void spaces between adsorbent particles. The selective pore volume and the non-selective void volume are generally expressed in volumetric quantities and are of importance in determining the proper flow rates of fluid required to be passed into an operational zone for efficient operations to take place for a given quantity of adsorbent.

When adsorbent "passes" into an operational zone (hereinafter defined and described) its non-selective void volume together with its selective pore volume carries fluid into that zone. The non-selective void volume is utilized in determining the amount of fluid which should pass into the same zone in a countercurrent direction to the adsorbent to displace the fluid present in the non-selective void volume. If the fluid flow rate passing into a zone is smaller than the non-selective void volume rate of adsorbent material passing into that zone, there is a net entrainment of liquid into the zone by the adsorbent. Since this net entrainment is a fluid present in non-selective void volume of the adsorbent, it in most instances comprises less selectively retained feed components.

The selective pore volume of an adsorbent can in certain instances adsorb portions of raffinate material from the fluid surrounding the adsorbent since in certain instances there is competition between extract material and raffinate material for adsorptive sites within the selective pore volume. If a large quantity of raffinate material with respect to extract material surrounds the adsorbent, raffinate material can be competitive enough to be adsorbed by the adsorbent.

Feed stocks which can be used in the process of this invention will be hydrocarbon fractions having a carbon number range of from about 6 carbon atoms per molecule up to about 30 carbon atoms per molecule. Typically, the carbon number range of the hydrocarbon fractions will be rather narrow, such as from about three to about ten carbon numbers. A $C_{10}$ to $C_{15}$ kerosine fraction or a a $C_{10}$-$C_{20}$ gas oil fraction) is a typical feed stream. Feed streams will contain normal paraffins, isoparaffins and aromatics in varying concentrations but little or no olefins. Depending on the type of crude from which the hydrocarbon fraction is derived and the carbon number range of the fraction, the normal paraffin concentration will typically range from about 15 to about 60 vol. % of the feed and the aromatic concentration from about 10 to about 30 vol. % of the feed. There may be more unusual feed streams which have aromatic concentrations of only about 2 to about 4 vol. % of the feed stream. Since the feed aromatics, like the isoparaffins, cannot enter the pores of adsorbent used in this process because their cross-sectional diameter is too great, almost all of the aromatics appear in the raffinate stream. A small portion, however, is rather tenaciously adsorbed on the surfaces of the adsorbent particles and ultimately appears as a contaminant in the extract (normal paraffin) product. The feed aromatics can include monocyclic aromatics such as benzene or alkylbenzenes; indanes or alkylindanes; and bicyclic aromatics including naphthalenes, biphenyls, or the acenaphthenes. The abovementioned aromatic contaminants can be generally characterized as having the general formula of $C_nH_{2n-J}$, where J as used in the mass spectrometer art, indicates a specific number which when supplied in the above-mentioned empirical formula can allow distinctive characterization of complicated aromatic types. We have found that certain $J_6$ and $J_{12}$ aromatic hydrocarbons are those which are most strongly held on the adsorbent. Other types of aromatic hydrocarbons such as the $J_8$ or $J_{10}$ or even $J_{16}$ type hydrocarbons would also be strongly adsorbed.

The sweeping agent, previously defined, will preferably have a boiling point which differs sufficiently from the boiling point of the feed stream raffinate component to be readily separated from the raffinate stream by subsequent distillation. Thus in this process the sweeping agent may be selected from the higher or lower boiling homologs of the isoparaffins or naphthenes in the feed stock. As a specific instance, a suitable sweeping agent which may be used in the separation of normal paraffins from a $C_{10}$ to $C_{15}$ feed stock is isooctane which is not adsorbed by the adsorbent and which is separable from the $C_{10}$–$C_{15}$ raffinate components by distillation.

The sweeping agent is supplied at a rate sufficient to substantially equal the volume of void space between the particles of adsorbent passing a given point in the process cycle at a given rate of circulation, thereby substantially and continuously removing the entrained material, primarily raffinate components, from between the particles of adsorbent as the latter is circulated through the process flow. The displaced raffinate components join the fluid stream flowing through the adsorbent and are eventually removed from the circulating fluid phase by withdrawal as the raffinate output stream at least a portion of which is then passed to a raffinate stream fractionation means where raffinate components can be recovered. The preferred rate of charging the sweeping agent in the purification zone is at a rate of flow equal to or greater than the rate of flow of the void spaces between the particles of adsorbent, a rate which is dependent in any particular instance upon the particle size of the adsorbent, whether a moving bed or fixed bed process is used, and other factors.

The desorbent materials used in the process of this invention should be materials that are easily separated from the feed mixture. Both the raffinate stream and the extract stream are removed from the adsorbent in admixture with desorbent materials. Without a method of separating these desorbent materials the purity of the extract components and the raffinate components if their recovery is desired would not be very high nor would the desorbent materials be available for reuse in the process. It is contemplated therefore that the desorbent materials will have a different boiling range than the feed mixture fed to the adsorbent which would allow fractionation to be used to separate the raffinate and extract components and allow recovery of the desorbent materials for possible reuse in the process.

In this process one or two desorbent materials can be employed. A first desorbent material will be optionally employed when it is desired to produce an extract product containing a reduced concentration of feed aromatics. By employing a first desorbent material the concentration of feed aromatics in the extract product can be reduced to less than about 0.05 wt. %. First desorbent materials which can be used in this process will comprise an aromatic hydrocarbon which has a different boiling point than the feed mixture to permit separation therefrom by distillation. The first desorbent material will also preferably have a boiling point different from the sweeping agent to permit separation therefrom by distillation. First desorbent materials which can be used in this process can comprise individual aromatics such as benzene, toluene, the xylene isomers, and ethylbenzene or a mixture of $C_8$ aromatics. In the example previously given where normal paraffins were to be separated from a $C_{10}$–$C_{15}$ feed stream and isooctane was used as the sweeping agent, para-xylene or ethylbenzene would be examples of suitable first desorbent materials. Where the first desorbent mixture is used in admixture with the sweeping agent, the concentration of the first desorbent material in the mixture can range from about 5 to near 100 vol. % of the total mixture. More preferably the concentration will be in the range of from about 15 to about 40 vol. %. Since the function of the first desorbent material is to desorb only the surface-adsorbed feed aromatics, it is also important that the first desorbent material contain little or no second desorbent material to avoid desorbing the normal paraffins. Preferably the concentration of second desorbent material in the first desorbent material will be less than about 1.0 vol. %.

The second desorbent material will comprise any normal paraffin having a boiling point different than that of the feed mixture to permit separation therefrom by distillation. A second desorbent comprising normal pentane is frequently used since it is easily separable from feed stocks generally used in this process. The second desorbent material can be 100% normal paraffins or can be lesser concentrations of normal paraffins in admixture with an isoparaffin or naphthene diluent. When used in admixture with a diluent the concentration of normal paraffins will typically be from about 40 to about 80 vol. % of the mixture. It is important that the second desorbent material contain little or no first desorbent material since the presence of aromatics hinders the desorption of normal paraffins by the second desorbent material. Preferably the concentration of first desorbent material in second desorbent material will be less than about 0.1 vol. %.

Solid adsorbents contemplated for use herein shall comprise shape-selective zeolites commonly referred to as molecular sieves. The term "shape selective" refers in the zeolite's ability to separate molecules according to shape or size because of zeolite's pores of fixed cross-sectional diameters. The zeolites belong to a group of aluminum silicate crystals having a framework structure in which every tetrahedron of $SiO_4$ or $AlO_4$ shares all its corners with other tetrahedra, thus accounting for all the silicon, aluminum and oxygen atoms in the structure. These crystals have a chemical formula in which the ratio (Si+Al):(O) is 1 to 2. Of the several types of known zeolites, only those having rigid frameworks are suitable molecular sieves. When originally formed the zeolite crystals contain water in the interstices defined by the framework. On moderate heating this water can be driven off and the open interstices are then of uniform size and can admit compounds whose maximum critical molecular diameters are not substantially greater tha the minimum diameters of the interstices. The pure zeolite molecular sieves, particularly the synthetic ones, generally are produced in the form of soft, powdery masses of small crystals. For use in commercial processes these zeolite crystals may be composited with binder materials such as clays, alumina or other materials, to form stronger, more attrition-resistant particles.

Adsorbents contemplated for use in this process will comprise zeolites having uniform pore diameters of 5 Anstroms such as chabazite or particularly such as Linde's commercially-available type 5A molecular sieve. As obtained commercially this latter material is usually in the form of an extrudate or a pellet or in granular form and contains pure 5A zeolite and a binder material such as clay. The adsorbent utilized in this process will generally be in the form of particles having a particule size range of from about 20 to about 40 mesh size.

The adsorbent may be employed in the form of a dense compact fixed bed which is alternatively contacted with the feed mixture and desorbent materials. In the simplest arrangement the adsorbent could be employed in the form of a single static bed. In another arrangement a set of two or more static beds could be employed with appripriate valving so that the feed mixture would pass through one or more adsorbent beds while a desorbent material would pass through one or more of the other beds in the set. The flow of feed mixture and desorbent materials may be either up or down through the desorbent. Any other conventional apparatus employed in static bed fluid-solid contacting may also be used.

Countercurrent moving-bed or simulated moving-bed countercurrent flow systems, however, have a much greater separation efficiency than fixed adsorbent bed systems and are therefore preferred. In the moving-bed or simulated moving-bed processes the adsorption and desorption operations are continuously taking place which allows both continuous production of an extract and a raffinate stream and the continual use of feed and desorbent streams. One preferred embodiment of this process utilizes what is known in the art as the simulated moving-bed countercurrent flow system. The operating principles and sequence of such a flow system are described in U.S. Pat. No. 2,985,589. In such a system it is the progressive movement of multiple liquid access points down an adsorbent chamber that simulates the upward movement of adsorbent contained in the chamber. Typically four of the access lines are active at any one time; the feed input stream, desorbent inlet stream, raffinate outlet stream, and extract outlet stream access lines. Coincident with this simulated upward movement of the solid adsorbent is the movement of the liquid occupying the void volume of the packed bed or adsorbent. So that countercurrent contact is maintained, a liquid flow down the adsorbent chamber may be provided by a pump. As an active liquid access point moves through a cycle the chamber circulation pump moves through different zones which require different flow rates. A programmed flow controller may be provided to set and regulate these flow rates.

The active liquid access points effectively divided the adsorbent chamber into separate zones, each of which has a different function. In my process it is generally necessary that three separate operational zones be present in order for the process to take place although in some instances an optional fourth zone may be used.

The adsorption zone, zone 1, is defined as the adsorbent located between the feed inlet stream and the raffinate outlet stream. In this zone, the feed stock contacts the adsorbent, an extract component is adsorbed, and a raffinate stream is withdrawn. Since the general flow through zone 1 is from the feed stream which passes into the zone to the raffinate stream which passes out of the zone, the flow through this zone is considered to be a downstream direction when proceeding from the feed inlet to the raffinate outlet streams.

Immediately upstream with respect to fluid flow in zone 1 is the purification zone, zone. 2. The purification zone is defined as the adsorbent between the extract outlet stream and the feed inlet stream. The basic operations taking place in zone 2 are the displacement from the non-selective void volume of the adsorbent of any raffinate material carried into zone 2 by the shifting of adsorbent into this zone and the selective desoption of any raffinate material adsorbed within the selective pore volume of the adsorbent or adsorbed on the surfaces of the adsorbent particles. These operations can best be effected by the use of a sweeping agent, a first desorbent material, and a portion of extract stream material passing out of zone 3 into zone 2 at zone 2's upstream boundary, the extract outlet stream. The flow of material in zone 2 is in a downstream direction from the extract outlet stream to the feed inlet stream.

Immediately upstream of zone 2 with respect to the fluid flowing in zone 2 is the desorption zone or zone 3. The desorption zone is defined as the adsorbent between the desorbent inlet and the extract outlet stream. The function of the desorption zone is to allow a second desorbent material which passes into this zone to displace the normal paraffins which were adsorbed upon the adsorbent during a previous contact with feed in zone 1 in a prior cycle of operation. The flow of fluid in zone 3 is essentially in the same direction as that of zones 1 and 2.

In some instances an optional buffer zone, zone 4, may be utilized. This zone, defined as the adsorbent between the raffinate outlet stream and the desorbent inlet stream, if used, is located immediately upstream with respect to the fluid flow to zone 3. Zone 4 would be utilized to conserve the amount of desorbent utilized in the desorption step since a portion of the raffinate. stream which is removed from zone 1 can be passed into zone 4 to displace desorbent material present in that zone out of that zone into the desorption zone. Zone 4 will contain enough adsorbent so that raffinate material present in the raffinate stream passing out of zone 1 and into zone 4 can be prevented from passing into zone 3 thereby contaminating extract stream removed from zone 3. In the instances in which the fourth operational zone is not utilized the raffinate stream passed from zone 1 to zone 4 must be carefully monitored in order that the flow directly from zone 1 to zone 3 can be stopped when there is an appreciable quantity of raffinate material present in the raffinate stream passing from zone 1 into zone 3 so that the extract outlet stream is not contaminated.

A cyclic advancement of the input and output streams through the fixed bed of adsorbent can be accomplished by utilzing a manifold system in which the valves in the manifold are operated in a sequential manner to effect the shifting of the input and output streams thereby allowing a flow of fluid with respect to solid adsorbent in a countercurrent manner. Another mode of operation which can effect the countercurrent flow of solid adsorbent with respect to fluid involves the use of a rotating disc valve in which the input and output streams are connected to the valve and the lines through which feed input, extract output, desorbent input, raffinate product recycle and raffinate output streams pass are advanced in the same direction through the adsorbent bed. Both the manifold arrangement and disc valve are known in the art. Specifically rotary disc valves which can be utilized in this operation can be found in U.S. Pat. Nos. 3,040,777 and 3,422,848. Both of the aforementioned patents disclose a rotary type connecion valve in which the suitable advancement of the various input and output streams from fixed sources can be achieved without difficulty.

In many instances, one operational zone will contain a much larger quantity of adsorbent than some other operational zone. For instance, in some operations the buffer zone can contain a minor amount of adsorbent as compared to the adsorbent required for the adsorption and purification zones. It can also be seen that in instances in which desorbent is used which can easily desorb extract material from the adsorbent that a relatively small amount of adsorbent will be needed in a desorption zone as compared to the adsorbent needed in the buffer zone or adsorption zone or purification zone or all of them. Since it is not required that the adsorbent be located in a single column, the use of multiple chambers or a series of columns is within the scope of the invention.

It is not necessary that all of the input or output streams be simultaneously used, and in fact, in many instances some of the streams can be shut off while others effect an input or output of material. The apparatus which can be utilized to effect the process of this invention can also contain a series of individual beds connected by connecting conduits upon which are placed input or output taps to which the various input or output streams can be attached and alternately and periodically shifted to effect continuous operaton. In some instances, the connecting conduits can be connected to transfer taps which during the normal operations do not function as a conduit through which material passes into or out of the process.

Reference can be made to the Description of the Drawing section of this specification, to D. B. Broughton U.S. Pat. No. 2,985,589, and to a paper entitled "Continuous Adsorptive Processing—A New Separation Technique" by D. B. Broughton presented at the 34th Annual Meeting of the Society of Chemical Engineers at Tokyo, Japan on Apr. 2, 1969, for further explanation of the simulated moving-bed countercurrent process flow scheme.

Although both liquid and vapor phase operations can be used in many adsorptive separation processes, liquid-phase operation is preferred for this process because of the lower temperature requirements and because of the higher yields or normal paraffin product that can be obtained with liquid-phase operation over those obtained with vapor-phase operation. Adsorption conditions will include a temperature range of from 40° to about 250° C. and a pressure range of from about atmospheric to about 500 psig to insure liquid phase. Desorption conditions will include the same range of temperature and pressures as used for adsorption conditions.

At least a portion of the extract output stream from zone 3 will pass to a first or extract-output-stream fractionation means for fractionation at first fractionation conditions into an overhead stream, a sidecut stream and a bottoms stream. The overhead stream will contain second desorbent material and sweeping agent and, when a first desorbent material is used in the process, preferably less than about 0.1 vol. % of the first desorbent material. The sidecut stream will contain sweping agent, a lower concentration of second desorbent material than is the overhead stream and, if first desorbent material is used, first desorbent material. The bottoms stream will be the extract product or normal paraffins and will be substantially free of desorbent materials or sweeping agent.

Likewise at least a portion of the raffinate output stream will pass to a second or raffinate-output-stream fractionation means where it will be fractionated at second fractionation conditions into an overhead stream, a sidecut stream and a bottoms stream. The overhead stream will contain second desorbent material and sweeping agent and, when a first desorbent material is used in the process, preferably less than about 0.1 vol. % of the first desorbent material. The sidecut stream will contain sweeping agent, a lower concentration of second desorbent than is in the overhead stream and if first desorbent material is used, first desorbent material. The bottoms will be the raffinate product (primarily isoparaffins and aromatics) and will preferably be substantially free of desorbent materials or sweeping agent. The term "substantially free" shall mean that the concentration of desorbent material in either the extract product of the raffinate product shall be less than about 5 vol. % and more preferably less than 1 vol. %.

The two sidecut streams will be combined and directed to a third fractionation means wherein the mixture will be fractionated at fractionation conditions to produce an overhead stream which will be recycled back to zone 3 and a bottoms stream which will be recycled back to zone 2. The overhead stream will contain second desorbent material and sweeping agent and, when a first desorbent material is used, preferably less than about 0.1 vol. % of the first desorbent material. The bottoms stream will contain sweeping agent, preferably less than 1.0 vol. % of the second desorbent material and, when a first desorbent material is used, first desorbent material. By removing sidecut streams from the first and second fractionation means, each containing reduced concentrations of second desorbent material as compared to the concentrations of second desorbent material in the respective overhead streams, and by passing these sidecut streams to the third fractionation means, the size and energy requirement of the third fractionation means can be reduced over those that would be required if no sidecuts were withdrawn and instead the overhead stream from the first or second fractionation means (or both or a portion of each) was directed to the third fractionation means. By my process considerably less second desorbent material passes to third fractionation means per unit of time thus permitting the reduction in the capital expense and operating expense of the third fractionation means. The first, second and third fractionation means will typically be fractionation columns, the design and operation of which is well known to the separation art.

The size of the units which can utilzie the process of this invention can vary anywhere from those of pilot-plant scale to those of commercial design and can range in flow rates from as little as a few cc. an hour up to many thousands of gallons per hour.

DESCRIPTION OF THE DRAWING

The attached drawing illustrates schematically one embodiment of the process of this invention. Basically the drawing shows four separate operating zones and three separate fractionation means along with input and output streams and connecting conduits. Adsorption zone 1, purification zone, 2, desorption zone 3, and optional buffer zone 4 are used to separate normal paraffins from isoparaffins to produce an extract output stream and a raffinate output stream. Fractionation means 15 and 19 are used to separate a desorbent material and a sweeping agent from the extract and raffinate output streams to produce an extract product stream and a raffinate product stream. Fractionation means 24 is used to separate a desorbent material from a sweeping agent for the reuse of each in an operating zone.

The four zones are stationary beds of solid adsorbent particles but may in other instances consist of a series of one or more individual chambers connected in a serial manner. Each of the individual zones may be single chamber or a series of beds stached upon one another in a column making up a zone. Thus in some instances each of the above zones would contain the same general quantity of adsorbent and have the same general physical dismensions, but in other instances some zones may require more adsorbent than other zones. The indicated overall net liquid flow through the zones is in a downward direction but in some instances a zone may be operating in a manner to allow flow of fluid for a certain period of time in a direction opposite to the overall net flow of fluid. The adsorbent particle flow can be considered to be in an upward direction to help in understanding the processing steps taking place in various zones. During normal fixed-bed countercurrent operations the adsorbent material remains stationary and the individual adsorption, purification, desorption and buffer zones, as defined, are moved through the adsorbent by shifting various input and output streams in a unidirectional manner to allow fluid to flow in a countercurrent direcion with respect to solid adsorbent and to continuously produce extract and raffinate streams. In most instances the shifting of the input and output streams along the fixed bed or adsorbent is done simultaneously and in the same dstance along the bed of adsorbent. In other instances it is desired that two or more zonal functions take place in the adsorbent between two input and output streams before the input and output streams are shifted.

In accordance with the definition of the zones previously given, the adsorption zone 1 is the adsorbent material located between feed input stream 6 and raffinate stream output stream 5 which is connected to zone 1 via line 11. Purification zone 2 is located immediately upstream from adsorption zone 1 and shares the feed input stream 6 as a common boundary with adsorption zone 1. Purificaton zone 2 is the adsorbent located between the extract outlet stream 8 and feed input stream 6. Immediately upstream from the purification zone 2 is desorption zone 3 which shares the extract outlet stream 8 as a common boundary with purification zone 2. Desorption zone 3 is the adsorbent between extract outlet stream 8 and desorbent inlet stream 9. Immediately upstream from desorption zone 3 is optional buffer zone 4 which shares the desorbent inlet stream 9 as a common boundary with desorption zone 3 and shares raffinate outlet stream 5 as a common boundary with purification zone 1. Optional zone 4 is the adsorbent located between desorbent inlet stream 9 and raffinate output stream 5.

Terminal zones 1 and 4 are connected by connecting conduits 10 and 11. The connecting conduits allow a portion of the fluid flowing out of zone 1 via line 11 to eventually flow via line 10 into zone 4 or zone 3 depending whether or not the optional zone is utilized, thereby allowing a closed-loop circulation of fluid. Lines 12, 13 and 14 are other connecting conduits connecting, respectively, zones 1 and 2, zones 2 and 3 and zones 3 and 4 to allow a continuous passge of fluid from one zone to and through all the other zones. Specifically, the material passing out of the adsorption zone 1 via line 11 can pass into line 5 or a portion of it may be diverted via line 10 to be passed eventually into buffer zone 4. Feed stock which passes into the process via line 6 passs through connecting conduit 12 and into the adsorption zone 1. In some instances a portion of the fluid material which passes out of purification zone 2 via line 12 may pass in admixture with feed material, entering the process via line 6, into adsorption zone 1. Line 13 is a connecting conduit which allows, in some instances, a porion of the fluid material withdrawn from desorption zone 3 via line 13 to bypass line 8 and pass via line 13 into purification zone 2. In a similar manner line 14 connects buffer zone 4 and desorption zone 3 and a portion of the fluid material leaving buffer zone 4 is allowed to pass out of that zone, to contact material passing into the process via desorbent input stream line 9 and to pass in admixture with desorbent through line 14 into the desorption zone 3. This allows a reductin in process desorbent requirements from external sources — namely, desorbent input stream line 9. Line 10 can contain a pump or other fluid displacement means in order to induce flow in the process in a direction passing from line 11 through line 10 and into buffer zone 4.

Other pumps and valves located on the input and output lines and the lines which connect the various zones which control flow into, out of and through the process are not shown. It is presumed they could be located where necessary by one skilled in the art to induce and conrol proper fluid flow in the process. The input streams passing into the various zones can be connected to high pressure sources or pumping means in order to induce flow into the process and the streams which pass out of the process can be regulated by back pressure valves in order to maintain regulated pressure drops through the zones to induce fluid flow. In some instances unidirectional flow directing devices such as check valves can be located on the conduits between the various zones where a pump around circuit is not utilized.

A feed input stream passes into the process and zone 1 via line 6, and since the overall general direction of fluid flow within that zone is in upward direction, passes through line 12 along with any material which may pass out of zone 2 via line 12 into zone 1.

As feed is passed into zone 1 an equal volume of raffinate stream material is displaced from zone 1 leaving that zone via line 11. A portion or all of the raffinate stream which passes through line 11 may be removed from zone 1 via line 5 with any portion not removed passing through line 10 into either zone 3 or zone 4 depending upon whether or not optional zone 4 is used in the process. Raffinate output stream line 5 is directed to fractionation means 19, hereinafter discussed in more detail, wherein desorbent material and sweeping agent are separated from raffinate components.

The adsorbent in zone 1 may be envisioned as moving in a direction countercurrent to the fluid flow in the zone. A simulated flow of solids occurs into and out of the adsorption zone when the zones are shifted during a portion of the entire cycle of operations. The adsorbent entering zone 1 comes from zone 3 or zone 4 depending upon whether or not optional zone 4 is used in the process. If optional zone 4 is not employed then the adsorbent leaving zone 3 and entering zone 1 will generally contain desorbent material present in both the non-selective void volumes and the selective void volumes. In instances where zone 4 is employed then a portion of the raffinate stream can be passed via line 10 into zone 4 to displace desorbent material from the non-selective void volumes present in the adsorbent particles in zone 4 into zone 3 via line 14. The adsorbent which then passes from the buffer zone 4 into the adsorption zone 1 contains for the most part desorbent material located within the adsorbent particle's selective pore volume which the extract material is required to desorb in zone 1. Although not shown in the drawing, it is possible to have desorbent material essentially removed from the selective pore volumes by additionally contacting the adsorbent with relatively high purity raffinate material prior to the contacting of te adsorbent with the feed input stream at the upstream portion of the adsorption zone. This feature which is part of a process described in U.S. Pat. No. 3,715,409, is desirable in many systems because it has been found that the absence of desorbent in the adsorption zone enhances the ability of the adsorbent to selectively adsorb and retain the extract component relative to the raffinate component.

The adsorbent, in passing upwardly through the adsorption zone 1 from its downstream boundary towards its upstream boundary with respect to fluid flow in that zone, adsorbs extract material from the feed input stream. As the adsorbent passes out of the adsorption zone it contains extract material and some raffinate material located within the selected pore volume of the adsorbent and some raffinate material adsorbed on the adsorbent particle surfaces. The material present in the non-selective void volume of adsorbent is generally raffinate material with small portions of extract material from the feed stock which have not been adsorbed by the adsorbent. This adsorbent then passes into the purification zone 2 passing into that zone at its downstream boundary feed input stream line 6.

When the adsorbent passes into the purification zone 2 from the adsorption zone 1, it generally contains some raffinate material present in the adsorbent's selective pore volume, in the non-selective void volume, and adsorbed on the surfaces of the adsorbent particles. The function of purification zone 2 then is to eliminate raffinate material from both the adsorbent's selective pore volume, the adsorbent's non-selective void volume and the adsorbent particle surfaces so that the adsorbent leaving the purification zone via its upstream boundary (line 8) contains as little raffinate material as possible which could contaminate the extract product stream. These functions are achieved in zone 2 in different ways. First, a portion of the extract stream, a mixture of desorbent and extract material, passes into purifaction zone 2 from zone 3 via line 13 and displaces any raffinte material from the adsorbent's selective pore volume and sweeps displaced raffinate material and raffinate material from the adsorbent's non-selective pore volume downwardly in the descending fluid stream toward the raffinate outlet stream line 5. As shown in the drawing the purification zone also has passing into it line 7 though which flows a raffinate-type sweeping agent. The sweeping agent itself supplements the washing action of the portion of the extract stream flowing into zone 2 from zone 3 via line 13. The sweeping agent also may permit removal of the feed raffinate material from the adsorbent while reducing the quantity of extract stream flowing into zone 2. A reduction in desorbent material, contained as part of the extract stream entering zone 2, enhances the adsorbent's ability to adsorb the last traces of extract material from the fluid surrounding the adsorbent in the purification zone. Additionally the sweeping agent, being a relatively non-adsorbed raffinate type material does not increase the load on the adsorbent in zone 1 of the process cycle and therefore does not reduce the capacity of the adsorbent for fresh extract material entering zone 1 via line 6 as is the case with the flow of extract stream from zone 3 into zone 2 via line 13. Reasonable flow rates of the sweeping agent or the extract stream, however, do not significantly remove the relatively small amount of raffinate material that is rather tenaciously adsorbed on the surface of the adsorbent particles. While the bulk of the aromatic hydrocarbons entering the process with the feed stream pass out of the process as part of the raffinate output stream via line 5, a small portion of these aromatics are adsorbed on the adsorbent particles in zone 1, pass with the adsorbent through zone 2 and are desorbed by desorbent material in zone 3 and appear as a contaminant in the extract stream which leaves the process via line 8. For this reason, in another embodiment of my invention a first desorbent material in admixture with the sweeping agent enters zone 2 via line 7. By contacting the adsorbent in zone 2 with the first desorbent material the surface-adsorbed aromatic contaminants are desorbed from the adsorbent particles and pass, with the aid of the sweeping agent and the portion of the extract stream entering zone 2 via line 13, downstream through zone 2 toward the raffinate outlet stream line 5. The first desorbent material is chosen to be specific for contaminant aromatic desorption only and not the desorption of the normal paraffin extract material. Thus the adsorbent which passes upwardly out of zone 2 into zone 3 contains normal paraffins in the selective pore volume and a much-reduced concentration of contaminant aromatics on the surfaces of the adsorbent particles. Although line 7 may be placed anywhere along the adsorbent material located in zone 2 from its most upstream location at extract output stream line 8 to its most downstream location at feed input sream line 6, it is preferred that line 7 be located more closely contiguous to the exract output stream line 8 so that the sweeping agent or mixture of sweeping agent and the first desorbent material can flow through most of the length of the zone and perform their respective functions. It is possible to regulate the fluid flow through zone 2 by controlling the quantity of material passing into this zone via line 7, the material passing into this zone from zone 3 via line 13, and the amount of material passing out of the lowest portion of the zone 2 via line 12.

The adsorbent which passes out of purification zone 2 passes into desorption zone 3 via that zone's downstream boundary, extract output stream line 8. The operation taking place in the desorption zone is essentially the removal of normal paraffins from the adsorbent. The removal is effected by contacting the adsorbent with a desorbent material capable of displacing normal paraffins from the selective pore volume of the adsorbent. The desorbent input stream passes into desorption zone 3's upstream boundary via lines 9 and 14. At least a portion of the desorbed normal paraffins pass out of desorption zone 3 in admixture with this desorbent material via extract output stream line 8. Extract output stream line 8 will then pass to fractionation means 15 hereinafter discussed in more detail, wherein paraffins are separated from desorbent material. The adsorbent leaving desorption zone 3 contains desorbent material located at both the adsorbent's selective pore volume and non-selective void volume. The adsorbent then passes into optional buffer zone 4 entering zone 4 at its downstream boundary the desorbent material input stream line 9.

Optional zone 4 in this process can be used to both conserve the amount of desorbent used in the process and prevent the contamination of extract material by raffinate material components. When operational zone 4 is used, it is possible that a portion of the raffinate output stream which does not pass out of line 5 can be passed into zone 4 via lines 10 and 11 to displace desorbent material from the non-selective void volume of the adsorbent particles in zone 4 and push desorbent material out of optional zone 4 via line 14 into zone 3. Since the desorbent material passes into the process via line 9 is connected to conduit 14 which connects optional zone 4 with desorption zone 3, the desorbent material which is displaced from the adsorbent in optional zone 4 tends to reduce the requirements of desorbent material which has to pass through line 9 into the process. The soild adsorbent leaving zone 4 at its upstream boundary, the raffinate output stream line 5, contains essentially desorbent material in its selective pore volume with raffinate material present in the adsorbent's non-selective void volume.

In instances in which optional zone 4 is not utilized it isk possible to pass some of the raffinate stream from zone 1 directly into zone 3. In such instances it is required that the composition of the material which leaves zone 1 via line 11 and which bypasses line 5 contains essentially no raffinate material. The initial raffinate material withdrawn from zone 1 contains a very high concentration of desorbent material and can be passed from lines 10 and 11 into zone 3. The flow of raffinate output stream leaving the process via line 5 may be stopped during this. When the stream passing though lines 10 and 11 into zone 3 contains an appreciable quantity of raffinate material the flow into zone 3 via line 10 is stopped and the raffinate output stream is then withdrawn via line 5. While the raffinate materials are being withdrawn through line 5, an outside source of desorbent material can be passed into zone 3 via lines 9 or 10.

The input and output lines 5, 6, 7, 8 and 9 during normal operations carry the respective streams as described previously. In order to allow a continuous operation, it is necessary that the individual input and output streams each be shifted in the same direction and in most instances at the same time. By shifting the input and output stream thoughout the bed of adsorbent, together with requiring that the terminal zones (adsorption zone 1 and buffer zone 4 or desorption zone 3) have a connecting conduit, it is possible to continuously effect the individual operations taking place in the various zones. When the zones described above are being shifted by incremental amounts through stationary adsorbent material the adsorbent contacts in the following order, the adsorption zone, the purification zone, the desorption zone and the buffer zone respectively.

At least a portion of the extract output stream passes through line 8 to fractionation means 15 which is operated at fractionation conditions to produce an overhead stream which passes through line 16, a sidecut stream which passes through line 17, and a bottoms stream which passes through line 18.

At least a portion of raffinate output stream passes through line 5 to fractionation means 19 which is operated at fractionation conditions to produce an overhead stream which passes through line 20, a sidecut stream which passes through line 21, and a bottoms stream which passes through line 22.

The sidecut streams passing through lines 17 and 21 join and pass in admixture through line 23 to fractionation means 24. Fractionation means 24 is operated at conditions to produce an overhead stream which passes through line 25 and a bottoms stream which passes through line 7. The bottoms stream from fractionation means 24 is recycled back zone 2 through line 7. The overhead stream from fractionation means 24 passing through line 25 joins the overhead stream from fractionation means 15 passing through line 16 and the mixture of the two overhead streams passes through line 26. This mixture is in turn joined by the overhead stream from fractionation means 19 and the mixture of all three overhead streams passes through line 9 and is recycled back to zone 3 as the desorbent input stream.

First desorbent material, second desorbent material and sweeping agent from outside sources can be added to the process for initial process startup or for makeup purposes through lines 27,28 and 29, respectively.

EXAMPLE

This example is presented to illustrate the process of my invention and reference to particular operating conditions, flow rates and compositions is not intended to be a limitation of the scope and spirit of the claims attached hereto. The example is taken from the process specifications for a commercial unit designed to separate normal paraffin from a hydrotreated kerosine fraction.

Considering first the adsorption section of this process embodiment, this section employs a simulated countercurrent-flow fixed-bed contacting system and a rotary valve distributing device to effect the continuous contacting of a feed stream and desorbent materials with adsorbent maintained in particular zones and the continuous withdrawal of an extract and a raffinate output stream from adsorbent maintained in particular zones. The adsorbent to be used is 100 metric tons of Linde 5A Molecular Sieves which is to be loaded into two serially-connected chambers each divided into 12 identical beds. Each bed will contain a transfer tap to which will be attached a transfer line through which material can pass into or out of a bed in accordance with a predetermined cycle of operations. Cycle time for the rotary valve (or for one cycle of operations) will be 50 minutes. A four-zone system is to be utilized; zones 1, 2 and 3 will each contain 7 beds of adsorbent and zone 4 will contain 3 beds of adsorbent. Operating temperature and pressure of the adsorbent chamber is to be 177° and 350 psig respectively with adsorption and desorption operations being conducted in the liquid phase. To produce an extract product (normal paraffins) containing less than 0.05 wt. % feed aromatics, two desorbent materials are to be employed. The first desorbent material will be a mixture of $C_8$ aromatics which will pass into zone 2 in admixture with isooctane as a sweeping agent. The mixture passing into zone 2 will be about 70 vol. % isooctane and about 30 vol. % $C_8$ aromatics with a maximum of about 1 vol. % of the second desorbent material. During steadystate process operation the flow rate of this mixture will be 3164 barrels per stream day (BPSD). The second desorbent material will be normal pentane. A mixture of about 60 vol. % normal pentane and about 40 vol. % isooctane as a diluent and a maximum of 0.1 vol. % of the first desorbent material will pass into zone 3. During steady-state process operation the flow rate of this mixture will be 7154 BPSD. Other flow rates during steady-state process operation will be 5695 BPSD of the feedstream into zone 1, 7299 BPSD of the extract output stream from zone 3 and 8312 BPSD of the raffinate output stream from zone 1.

Considering now the fractionation and desorbent-recycle portion of the process embodiment, 7299 BPSD of extract output stream will be directed to an extract fractionation column which will be operated to produce 3836 BPSD of extract column overhead, 2116 BPSD of extract column sidecut and 1347 BPSD of extract column bottoms of extract product. The composition of the overhead will be 67.0 mol. % normal pentane and 33 mol. % isooctane; that of the sidecut will be 13.0 mol. % normal pentane, 73.6 mol. % isooctane and 13.4 mol. % $C_8$ aromatics and that of the extract product will be about 99 mol. % normal paraffins. The extract column will have an inside diameter of 1800 mm and will contain 50 valve-type trays at 600 mm spacing with the extract output stream being fed to tray 34 and the sidecut stream being removed from tray 20. Operating pressures will be about 20, 22 and 26 psig and operating temperatures will be about 101°, 122°, and 257° C. at the column top, sidecut tray and bottom respectively. A raffinate output stream flow rate of 8312 BPSD will be directed to a raffinate fractionation column which will be operated to produce 2516 BPSD of raffinate column overhead, 1438 BPSD of raffinate column sidecut and 4358 BPSD of raffinate column bottoms. The composition of the overhead will be 66.7 mol. % normal pentane and 33.3 mol. % isooctane; that of the sidecut will be 6.9 mol. % normal pentane, 42.9 mol. % isooctane and 50.2 mol. % $C_8$ aromatics and that of the bottoms will be 1.2 mol. % normal paraffins, 29.2 mol. % naphthenes, 45.0 mol. % feed isoparaffins and 24.6 mol. % feed aromatics. The raffinate column will have an inside diameter of 2200 mm and will contain 60 valve-type trays at 600 mm spacing with the raffinate output stream being fed to tray 38 and the sidecut stream being removed from tray 20. Operating pressures will be about 20, 22 and 27 psig and operating temperatures will be about 101°, 138° and 270° C. at the column top, sidecut tray and bottom respectively.

The extract column sidecut and the raffinate column sidecut along with 413 BPSD of a mixture of isooctane and $C_8$ aromatics used as a sealant for the rotary valve are passed in admixture to the desorbent splitter fractionation column which will be operated to produce 802 BPSD of splitter overhead and 3164 BPSD of splitter bottoms. The composition of the overhead will be 44.6 mol. % normal pentane and 45.4 mol. % isooctane while that of the bottoms will be 62.2 mol. % isooctane and 37.8 mol. % $C_8$ aromatics. The desorbent splitter column will have an inside diameter of 100 mm and will have 25 valve-type trays at 600 mm spacing with the column feed being fed to tray 16. Operating pressure will be about 25 and 29 psig and operating temperatures wil be about 119° and 156° C. for the column top and bottom respectively. The desorbent splitter column bottoms will be recycled back to zone 2 of the adsorption section and the desorbent splitter column overhead, together with the extract column overhead and the raffinate column overhead, will be recycled back to zone 3 of the adsorption section.

I claim as my invention:

1. In a process for the separation of normal paraffins from a feed stream comprising a mixture of normal paraffins and isoparaffins which process employs an adsorbent comprising a shapeselective zeolite and comprises the steps of:
   a. maintaining net fluid flow through a column of an adsorbent in a single direction, which column contains at least three zones having separate operational functions occuring therein and being serially interconnected with the terminal zones of said column connected to provide a continuous connection of said zones;
   b. maintaining an adsorption zone in said column, said zone defined by the adsorbent located between a feed input stream at an upstream boundary of said zone and a raffinate output stream at a downstream boundary of said zone;
   c. maintaining a purification zone immediately upstream from said adsorption zone, said purification zone defined by the absorbent location between an extract output stream at an upsteam boundary of said purification zone and said feed input stream at a downstream boundary of said purification zone, said purification zone having a sweeping agent input stream located upstream from said feed input stream;
   d. maintaining a desorption zone immediately upstream from said purification zone, said desorption zone defined by the adsorbent located between a desorbent input stream at an upstream boundary of said zone and said extract output stream at a downstream boundary of said zone;
   e. passing a sweeping agent comprising a raffinate-type compound into said purification zone;
   f. passing said feed stream into said adsorption zone at adsorption conditions to effect the selective adsorption of said normal paraffins by said adsorbent and withdrawing a raffinate output stream comprising isoparaffins, sweeping agent and a hereinafter described desorbent material from said adsorption zone;
   g. passing a desorbent material into said desorption zone at desorption conditions to effect the displacement of normal paraffins from the adsorbent in said desorption zone and withdrawing an extract output stream comprising normal paraffins, sweeping agent and desorbent material from said desorption zone;
   h. passing at least a portion of said extract output stream to a first fractionation means and therein fractionating at first fractionating conditions said extract output stream to produce a first overhead stream comprising a mixture of sweeping agent and desorbent material and a first bottoms fraction comprising normal paraffins;
   i. passing at least a portion of said raffinate output stream to a second fractionation means and therein fractionating at second fractionating conditions said raffinate output stream to produce a second overhead stream comprising a mixture of sweeping agent and desorbent material and a second bottom fraction comprising isoparaffins;

j. separating in a third fractionation means maintained at third fractionating conditions mixture of sweeping agent and desorbent material to produce a third overhead stream comprising desorbent material and a third bottoms fraction comprising sweeping agent;

k. recycling at least a portion of said third overhead stream to said desorption zone;

l. recycling at least a portion of said third bottoms fraction to said purification zone;

m. periodically advancing through said column of adsorbent particles in a downstream direction with respect to fluid flow in said adsorption zone the feed input stream, raffinate output stream, desorbent input stream and extract output stream to effect the shifting of zones through said mass of adsorbent and the production of extract output and raffinate output streams, wherein the improvement comprises a fractionating and recycle method which comprises the steps of:

i. removing a sidecut stream comprising sweeping agent and desorbent material from said first or second fractionation means, said sidecut stream containing a lower concentration of desorbent material than either said first overhead stream or said second overhead stream;

ii. passing at least a portion of said sidecut stream to said third fractionation means maintained at fractionating conditions and therein separating said sidecut stream to produce said third overhead stream and said third bottoms fraction, and iii. passing in admixture at least a portion each of said third overhead stream, said first overhead stream and said second overhead to said desorption zone.

2. The process of claim 1 further characterized in that said feed stream has a carbon number range of from about 6 to about 30 carbon atoms per molecule.

3. The process of claim 1 further characterized in that said zeolite is zeolite 5A.

4. The process of claim 1 further characterized in that it includes the step of maintaining a buffer zone immediately upstream from said desorption zone, said buffer zone defined as the adsorbent located between the desorbent input stream at a downstream boundary of said buffer zone and a raffinate output stream at an upstream boundary of said buffer zone.

5. The process of claim 1 further characterized in that said desorbent material comprises normal paraffins having a different boiling point than that of the normal paraffins in the feed stream.

6. The process of claim 1 further characterized in that said adsorption conditions and desorption conditions include a temperature within the range of from about 40° to about 250° C. and a pressure of from about atmospheric to about 500 psig.

7. In a process for the separation of normal paraffins from a feed stream comprising a mixture of normal paraffins, isoparaffins and aromatic hydrocarbons which process employs an adsorbent comprising 5A zeolite and comprises the steps of:

a. maintaining net fluid flow through a column of an adsorbent in a single direction, which column contains at least three zones having separate operational functions occurring therein and being serially interconnected with the terminal zones of said column connected to provide a continuous connection of said zones;

b. maintaining an adsorption zone in said column, said zone defined by the adsorbent located between a feed input stream at an upstream boundary of said zone and a raffinate output stream at a downstream boundary of said zone;

c. maintaining a purification zone immediately upstream from said adsorption zone, said purification zone defined by the adsorbent located between an extract output stream at an upstream boundary of said purification zone and said feed input stream at a downstream boundary of said purification zone, said purification zone having a sweeping agent input stream located upstream from said feed input stream;

d. maintaining a desorption zone immediately upstream from said purification zone, said desorption zone defined by the adsorbent located between a desorbent input stream at an upstream boundary of said zone and said extract output stream at a downstream boundary of said zone;

e. passing said feed stream into said adsorption zone at adsorption conditions to effect the selective adsorption of normal paraffins and aromatics by adsorbent in said zone;

f. passing into said purification zone a mixture of a first desorbent material and a sweeping agent and therein desorbing at first desorption conditions aromatics from the adsorbent;

g. withdrawing from said adsorption zone a raffinate output stream comprising feed isoparaffins and aromatic hydrocarbons, sweeping agent and first desorbent material;

h. passing a desorbent input stream comprising second desorbent material into said desorption zone and therein desorbing at second desorption conditions normal paraffins from the adsorbent;

i. withdrawing an extract output stream comprising normal paraffins, sweeping agent and second desorbent material from said desorption zone;

j. passing at least a portion of said extract output stream to a first fractionation means and therein fractionating at first fractionation condition said extract output stream to produce a first overhead stream comprising a mixture of sweeping agent, first desorbent material, and second desorbent material and a first bottoms fraction comprising normal paraffins;

k. passing at least a portion of said raffinate output stream to a second fractionation means and therein fractionating at second fractionating conditions said raffinate output stream to produce a second overhead stream comprising a mixture of sweeping agent, first desirbent material and second desorbent material and second bottoms fraction comprising isoparaffins and feed aromatics;

l. separating in a third fractionation means maintained at third fractionating conditions a mixture of sweeping agent, first desorbent material and second desorbent material to produce a third overhead stream comprising sweeping agent and second desorbent material and a third bottoms fraction comprising sweeping agent and first desorbent material;

m. recycling at least a portion of said third overhead stream to said desorption zone;

n. recycling at least a portion of said third bottoms fraction to said purification zone;

o. periodically advancing through said column of adsorbent particles in a downstream direction with respect to fluid flow in said adsorption zone the feed input stream, raffinate output stream, desorbent input stream and extract output stream to effect the shifting of zones through said mass of adsorbent and the production of extract output and raffinate output streams, wherein the improvement comprises a fractionating and recycle method which comprises the steps of:

i. removing a sidecut stream comprising sweeping agent and first desorbent material from said first or second fractionation means, said sidecut stream containing a lower concentration of second desorbent material than either said first overhead stream or said second overhead stream;

ii. passing at least a portion of said sidecut stream to said third fractionation means maintained at fractionating conditions and therein separating said sidecut stream to produce said third overhead stream and said third bottoms fraction; and, iii. passing a mixture of at least a portion each of said first overhead stream, said second overhead stream and said third overhead to said desorption zone.

8. The process of claim 7 further characterized in that said feed stream has a carbon number range of from about 6 to about 30 carbon atoms per molecule.

9. The process of claim 7 further characterized in that in includes the step of maintaining a buffer zone immediately upstream from said desorption zone, said buffer zone defined as the adsorbent located between the desorbent input stream at a downstream boundary of said buffer zone and a raffinate output stream at an upstream boundary of said buffer zone.

10. The process of claim 7 further characterized in that said adsorption conditions, first desorption conditions and second desorption conditions, include a temperature within the range of from about 40° to about 250° C. and a pressure of from about atmospheric to about 500 psig.

11. The process of claim 7 further characterized in that said first desorbent material comprises an aromatic hydrocarbon having a different boiling point than that of aromatic hydrocarbons in the feed stream.

12. The process of claim 11 further characterized in that said aromatic hydrocarbon is selected from the group consisting of benzene, toluene, ethylbenzene and the xylene isomers.

13. The process of claim 7 further characterized in that said first desorbent material comprises from about 5 vol. % to about 100 vol. % of the mixture of sweeping agent and first desorbent material passed into the purification zone.

14. The process of claim 7 further characterized in that said second desorbent materizal comprises normal paraffins having a different boiling point than that of the normal paraffins in the feed stream.

15. The process of claim 14 further characterized in that said second desorbent material comprises normal pentane.

16. The process of claim 7 further characterized in that said third bottom fraction, recycled to said purification zone, contains less than about 1 vol. % of said second desorbent material.

17. The process of claim 7 further characterized in that the mixture of said first, second and third overhead streams passed to said desorption zone contains less than about 0.1 vol. % of said first desorbent material.

18. The process of claim 7 further characterized in that said first bottoms fraction contains less than about 0.05 wt. % of feed aromatic hydrocarbons.

* * * * *